United States Patent
Suzuki et al.

(10) Patent No.: US 6,852,973 B2
(45) Date of Patent: Feb. 8, 2005

(54) SCANNING CHARGED PARTICLE MICROSCOPE

(75) Inventors: Hidekazu Suzuki, Chiba (JP); Atsushi Uemoto, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/410,224

(22) Filed: Apr. 9, 2003

(65) Prior Publication Data

US 2004/0021074 A1 Feb. 5, 2004

(30) Foreign Application Priority Data

Apr. 10, 2002 (JP) ........................................ 2002-108312

(51) Int. Cl.⁷ .............................................. G01N 13/16
(52) U.S. Cl. ...................... 250/306; 250/307; 250/310; 250/396 R
(58) Field of Search ................................ 250/310, 307, 250/397, 311, 306, 309, 396 ML, 396 R, 491.1

(56) References Cited

U.S. PATENT DOCUMENTS

| | | | | |
|---|---|---|---|---|
| 4,600,832 A | * | 7/1986 | Grund | 250/201.7 |
| 4,675,528 A | * | 6/1987 | Langner et al. | 250/396 R |
| 4,827,125 A | * | 5/1989 | Goldstein | 250/234 |
| 5,445,011 A | * | 8/1995 | Ghislain et al. | 73/105 |
| 5,557,156 A | * | 9/1996 | Elings | 310/316.01 |
| 5,627,373 A | * | 5/1997 | Keese | 250/310 |
| 6,621,082 B2 | * | 9/2003 | Morita et al. | 250/310 |

* cited by examiner

*Primary Examiner*—Nikita Wells
*Assistant Examiner*—Johnnie L Smith, II
(74) *Attorney, Agent, or Firm*—Adams & Wilks

(57) ABSTRACT

The present invention sets out to provide a scanning charged particle microscope equipped with a rapid control function capable of extrapolating an in-focus point from image information for a single frame and an automatic focusing system capable of reliably and precisely carrying out a focusing operation for a horizontal pattern image. The automatic focusing system provided in the scanning charged particle microscope of the present invention is provided with means for changing a focal point each raster scan line, and control means for comparing image information each scanning line and extrapolating focusing positions. The scanning line can then be made to be an inclined scanning line that is a combination of a horizontal component and a vertical component with respect to a chip array on a semiconductor wafer. Further, a method is adopted comprising a first step of reliably taking in a coarse in-focus point and a second step of detecting the in-focus point with a high degree of precision.

15 Claims, 4 Drawing Sheets

VERTICAL PATTERN

HORIZONTAL PATTERN

SCANNING CHARGED PARTICLE MICROSCOPE

BACKGROUND OF THE INVENTION

1. Field of the Invention

The present invention relates to a method and system for reliably, accurately and rapidly executing an automatic focusing function for a scanning charged particle microscope typified by an electron microscope, etc.

2. Description of Related Art

Tests are implemented using defect checking devices to detect defects such as the adhesion of foreign matter that are the main cause of defective device operation as a means of managing yield in semiconductor device manufacturing processes. The defect checking devices detect defects and store the number and position of these defects in a defect file for subsequent processes. Semiconductor device wafers are typically substantially circular plates as shown in FIG. 4. A lattice of a large number of the same chips 2 are transferred onto a single wafer 1. The checking device then scans the surface of the wafer manufactured in this manner using an optical probe so as to detect surface defects. When a defect is detected, a chip number (for example, a way of showing which row of which column) specifying at which chip the defect exists and internal chip coordinate information specifying the position within the chip are stored in memory as a data file. Monitoring and analysis of the defects is carried out by various microscopes and analysis apparatus based on this storage information and one of these is high resolution defect monitoring using an electron microscope for defect monitoring. During this time, positioning of the noted defects in the field of vision of the microscope is carried out based on storage information of the defect checking device. However, focal adjustment of the optical system of the microscope in order to observe the defects using an electron microscope are carried out by the electron microscope itself which is typically provided with an Auto Focus function.

Conventionally, a so-called "frame focusing control method" is widely adopted for these automatic focusing mechanisms. This frame focusing control method is a method whereby frame images are sequentially read in while moving the focal point and is based on the theory that a difference signal with neighboring pixels occurring at an outline portion is bigger for clearer images. A differential value is obtained for the image signal and the focal point is moved in a direction giving a larger value. An image expressing the maximum value is then traced or extrapolated and the in-focus point is obtained. However, a time on the order of three to ten seconds, depending on the application, is required in order to carry out the operation of taking in a large number of frame images while moving the focal point.

"Focal point adjustment methods occurring in charged particle beam device" was therefore proposed in Japanese Patent Laid-open Publication No. Hei. 7-16132 as a means for overcoming the fact that this control operation is too time-consuming. This reference discloses a focal point adjustment method for a charged particle beam device comprising a focusing lens for focusing a charged particle beam onto a sample, scanning means for scanning an irradiation position of the charged particle beam on the sample, a detector for detecting a signal obtained by irradiation of the sample with a charged particle beam, and means for sequentially changing the focusing of the charged particle beam on the sample. Here, the focusing of the charged particle beam is sequentially changed in synchronization with a vertical scanning signal and detection signals occurring for each focused state of the charged particle beam are accumulated with regards to signals detected by the detector. Each accumulated signal is then stored and an optimum focal point position is obtained from the stored series of accumulated values. The focusing lens is then set to the optimum focusing position. In this method, the focal point position is changed every time the vertical position of the scanning line changes rather than being changed once for every frame and image definition is compared for each scanning line. Control can therefore be implemented more rapidly compared with the related art where images are compared for every frame. However, in this method, there is a problem in that a pattern extending in a vertical direction of the sample image as shown in FIG. 1A is necessary in order to implement automatic focal point adjustment. If this is not present, it is not possible to perform a comparison of every scanning line. Namely, image definition for each scanning line can be discerned using the differences in image signals occurring at points passing through boundary regions. Therefore, when the image is a linear pattern going along the direction of the scanning lines as shown in FIG. 1B, the scanning lines do not pass through the boundary region and the focusing operation therefore does not operate with this method. In other words, the image information in the scanning direction in this case is uniform and difference signals for neighboring pixel information are therefore all zero. Semiconductor patterns differ from typical images taken of scenery or people in that vertical direction boundaries and horizontal direction boundaries are common, which means that such problems cannot be neglected in these kinds of situations.

SUMMARY OF THE INVENTION

The present invention provides a rapid control function capable of extrapolating an in-focus point from image information for a single frame and an automatic focusing system capable of reliably and precisely carrying out a focusing operation for a horizontal pattern image.

The automatic focusing system of the present invention is provided with means for changing a focal point for each raster scan line, and control means for comparing image information for each scanning line and extrapolating in-focus positions, with the scanning line being made to be an inclined scanning line that is a combination of a horizontal component and a vertical component with respect to a chip array on a semiconductor wafer. As means to implement this, there is a method carried out using beam deflection or a method of setting the stage in such a manner that the direction of the sample and the horizontal scanning direction intersect each other.

In order that peak values, i.e. in-focus points can be obtained even when the pattern shapes through which each of the scanning lines pass differ, control where image definition is compared each raster line and in-focus points are extrapolated is such that scanning sections are discriminated from changes in step shapes for between each scanning line and peak values from small consecutive changes between each scanning line are extrapolated.

Further, in order to implement automatic focal point control, a method is adopted comprising a first step of taking coarse in-focus points using coarsely taken large differences between focal points for between scanning lines, and a second step of detecting in-focus points with a high degree of precision using small differences in focal points between scanning lines based on the coarse in-focus point information.

There is therefore adopted a method for implementing automatic focusing control comprising the steps of: recording pre-selected in-focus points taking into consideration the pattern arrangement of semiconductor chips arrayed on the wafer and being capable of covering the entire region, accessing the in-focus points covering positions of noted defects obtained by a defect checking device and executing a focusing operation, and consecutively monitoring defects in positions covered by the in-focus points in the state of a focal position of a lens obtained at this time.

DETAILED DESCRIPTION OF THE INVENTION

The present invention provides a technology for performing more detailed checks using an electron microscope for defects such as those caused by foreign bodies becoming attached to some of the same chips arrayed in a lattice on a semiconductor wafer that are detected using a defect checking device, and as such it is important to acquire clearly defined images of defects constituting the subjects of such checks. The situation in the related art where related autofocusing methods were used to perform frame focusing control on image information for a plurality of frames was excessively time-consuming whatever the approach adopted. A method where the focal point is changed for every horizontal scanning line which switches vertical deflection so that image definition is compared for every scanning line to exert focusing control is therefore preferred. However, there is still occasionally the inconvenience that this does not operate very well with images for regions where the pattern only exists in the horizontal direction as described previously. The cause of this is the fact that a pattern extending in the vertical direction does not exist, so that the horizontal scanning lines do not pass through the boundary of the pattern and results are obtained where the image information is seen to be uniform. The present applicant therefore gave consideration to implementing scanning in an inclined direction, i.e. providing the microscope beam deflection mechanism with a scanning rotation function in order to ensure that the scanning lines always cross this horizontal pattern even when the image pattern is an interconnect portion extending along a boundary line of an element in a horizontal direction or extending in a horizontal direction.

If the direction of the scanning lines is at an incline, then boundary points are always passed through even if the pattern of the observed region is a vertical pattern or a horizontal pattern. Since patterns for chips arrayed on a semiconductor wafer in a vertical direction or horizontal direction are common, this autofocus function is effective, with the exception of occasional regions where there is no pattern.

Figure 5:
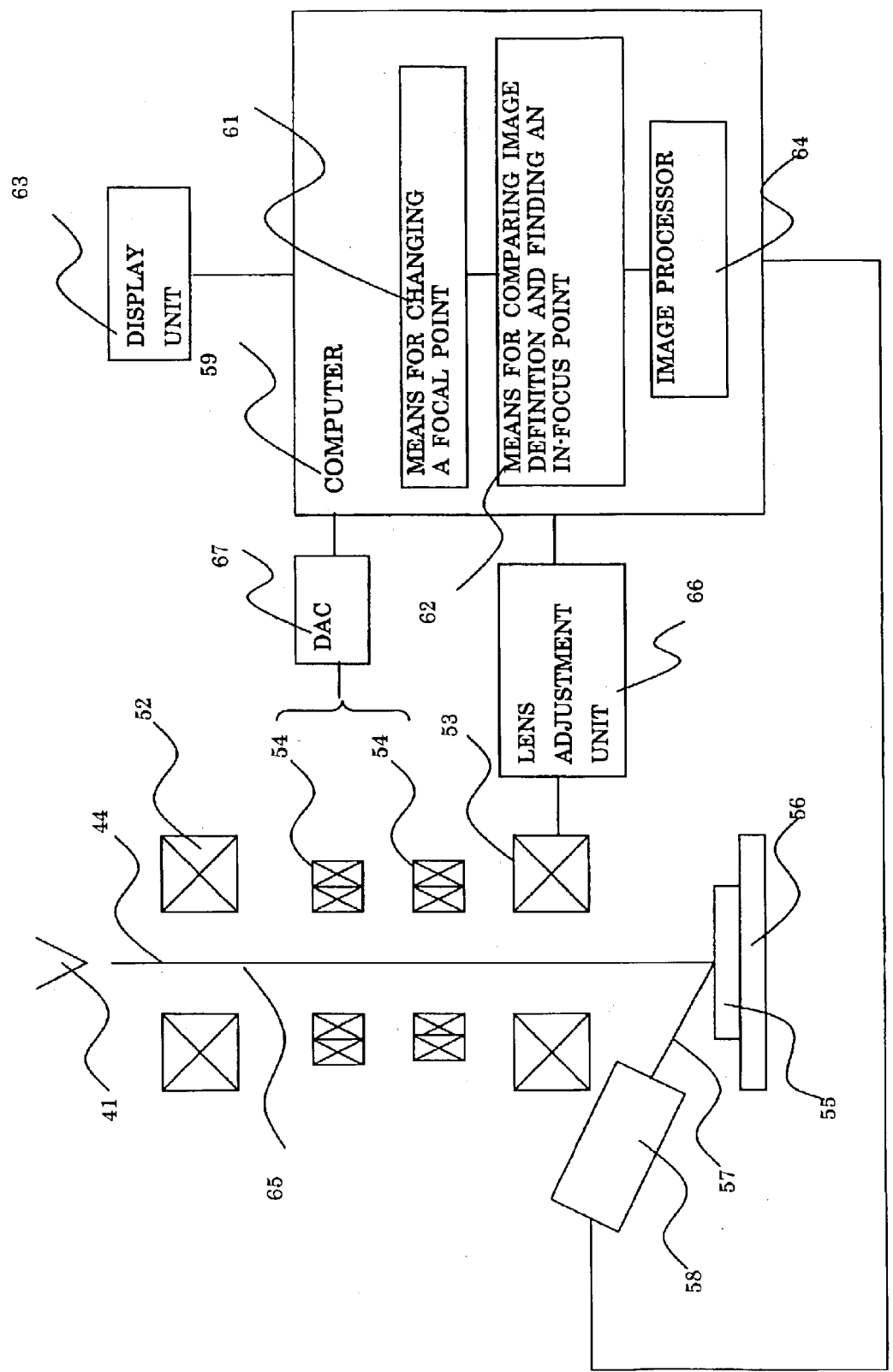
FIG. 5 is a scanning charged particle microscope having an automatic focusing system.

FIG. 5 shows a scanning charged particle microscope having an automatic focusing system of the present invention. Charged particle beam 65 generated by the charged particle source 41 is condensed by condenser lens 52. Deflector 54 deflects the charged particle beam condensed by the condenser lens 52 so as to make the charged particle beam scan the sample 55. The objective lens 53 focuses the charged particle beam 65 on the sample 55. The secondary electron detector 58 detects secondary electrons generated from the sample 55 owing to the irradiation of the charged particle beam 65. The image processor 64 processes signals from the secondary electron detector 58 and a sample image is displayed on the display unit 63.

Signals from the computer 59 make the DAC 67 change currents flowing in coils of an X-deflector and a Y-deflector comprising the beam deflector 54. Changing the currents in the coils of the X-deflector and Y-deflector enables a change in scanning direction of the charged particle beam in desired directions on the sample 55. Namely, for example, the charged particle beam is able to scan a semiconductor chip diagonally. It is possible to make the charged particle beam always scan across a stripe pattern whether the stripe pattern on the semiconductor is vertical or horizontal. In this condition, a focal distance of the objective lens 53 is changed for every scanning line, which is done via the lens adjustment unit 66 based on signals from "means for changing the focal distance 61" that is provided in the computer 59. The image obtained at every scanning line is taken into "means for comparing image definitions and finding an in-focus point 62" and image definitions are compared here. To compare the image definitions, the difference of image signals between a background and the stripe pattern obtained when the charged particle beam passes across the boundary of the stripe pattern and the background. The position where the maximum difference is obtained is judged as the position where the image is the clearest. And the position is judged as an in-focus point.

A description is now given of the theory of the present invention with reference to FIG. 1. The case of a pattern that is a vertical stripe at the sample surface is shown in FIG. 1A with each horizontal scan therefore passing through this vertical stripe without fail so that the image information changes substantially twice at the points where both boundaries are passed through. An image is acquired while sequentially changing the focal point of the electron beam every scanning line. Images where the focus differs respectively each scanning line are therefore composed. Of these images, images occurring at scanning lines at positions where the focus was correct are most clearly defined. The difference signals for between neighboring pixels at the boundary positions of these scanning lines therefore give the largest output. This focal point between scanning lines giving this maximum value is then the in-focus point. However, in the case of the horizontal stripe pattern at the sample surface shown in FIG. 1B, there is no intersection between each horizontal scanning line and this horizontal stripe. Rather than just regions where there is no pattern, even in pattern regions the scanning lines may scan along the pattern and therefore do not pass through a boundary. There is therefore no large change in the image information. As a result it is not possible to implement this kind of autofocus method where comparisons are made while shifting the focal point each scanning line for this kind of region.

Figure 1A:
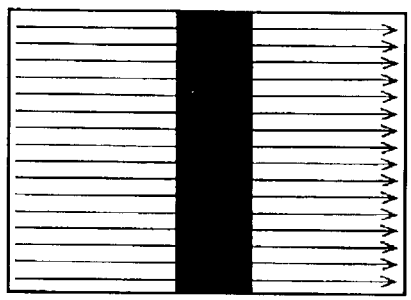
FIGS. 1A–1E are views illustrating the theory of the present invention using the relationship between the pattern on the sample surface and the beam scanning lines.
Figure 1B:
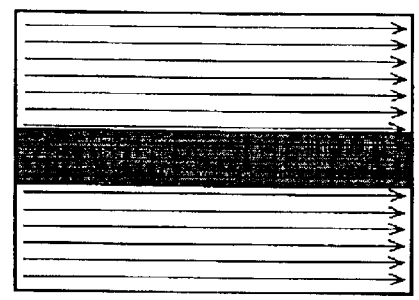
Figure 1B:
Figure 1C:
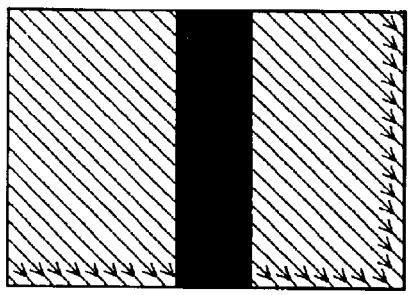
Figure 1C:
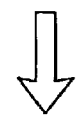
Figure 1D:
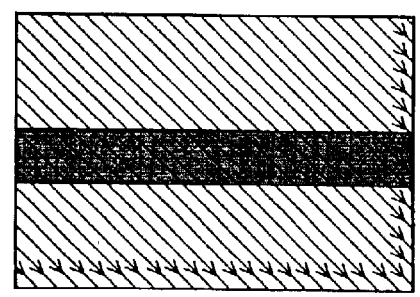

Therefore, in the present invention, the main scanning of the beam is given an angle of inclination with respect to the direction of the chip array, as shown in FIG. 1C and FIG. 1D. While scanning in this manner, sub-scanning is also carried out in a direction orthogonal to the main scanning direction and the focal point is changed every time the sub-scanning position is changed. As a result of scanning in this manner, at least some of the scanning lines will always pass through the pattern boundary even in the case of the vertical stripe pattern region shown in FIG. 1C or in the case of the horizontal stripe pattern region shown in FIG. 1D. By slightly changing the focal point of the electron beam each time the scanning line positions are changed for the scanning lines, it is possible to obtain an in-focus point or a position close to the focal point with any kind of scanning lines. Namely, when scanning commences and sequential sub-scanning proceeds, the difference signal for neighboring pixels becomes larger and the image gradually becomes more clearly defined. When the sub-scanning then progresses further, next, the difference signal for neighboring pixels becomes smaller and the image therefore gradually becomes less well defined. This peak position is then the in-focus point. When the difference signals for neighboring pixels becomes small as the sequential sub-scanning progresses, movement is in a direction away from the in-focus point. It is therefore necessary to change the direction of movement and when it is taken that the difference signal has been large all along up to the end of the sub-scanning, it is taken that the in-focus point does not exist within this width of changing the focal point. Scanning is then executed against from this focal point position so that a peak position is detected. This operation is essentially the same as the frame focusing control of the related art but differs in that rather than changing the position of the focal point every frame, the position of the focal point is changed for every scanning line. Further, the direction of the scanning lines is not horizontal but rather is inclined. By adopting this approach it is possible to ensure the rapidness of the focusing operation and to ensure a steady operation that is not influenced by the pattern shape.

Figure 1E:
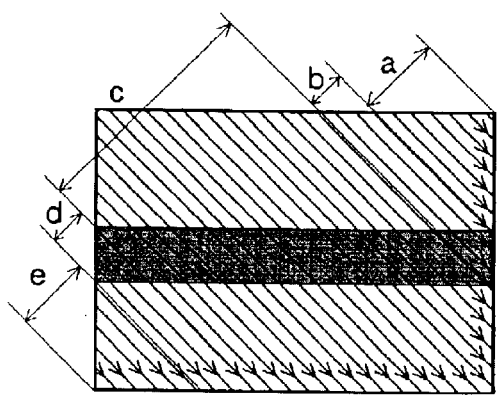

The pattern conditions are all the same as for that of the related art where definition is compared every frame but in the autofocus operation of the present invention, the pattern captured by each scanning line is not necessarily the same. That shown in FIG. 1A where a uniform vertical stripe pattern is scanned in the horizontal direction is given as an exceptional example where the pattern conditions are the same for all of the scanning lines. However, in the case of this invention, there may be a vertical pattern or there may be a horizontal pattern and the pattern conditions for each scanning line are not all the same. Looking at an example of the case where the inclined scanning method of the present invention is implemented on the horizontal stripe pattern shown in FIG. 1D, as shown in FIG. 1E, in a first scanning section a the scanning lines do not pass through the pattern. In a following scanning section b, a boundary from a plain-colored region to a pattern region is entered one time. In a middle scanning section c, a boundary from a plain-colored region to a pattern region is entered one time, and a boundary from a pattern region exiting to a plain colored region is passed through one time. Next, in a scanning section d, a boundary exiting from the pattern region to the plain-colored region is passed through one time. Finally, in a scanning section e, the scanning lines do not pass through the pattern. It can therefore be determined that comparisons of the scanning line images are meaningless in at least the scanning sections a and e where autofocus control does not function. At the scanning sections b and d, the directions of the changes in signal level have inverse relationships but if absolute value comparisons are made then the conditions become the same and comparison is possible. The conditions are the same within the scanning section c but the orientation of the change in signal level at the boundary upon entering the pattern region from the plain colored region and the orientation of the change in signal level at the boundary upon exiting from the pattern region to the plain colored region are opposite to each other and it is therefore preferable to add their absolute values. The number of times the boundaries are passed through at the scanning section c and the scanning sections b and d is different and a simple comparison is therefore meaningless. A corresponding relationship is therefore composed where the signals for the scanning sections b and d are doubled and compared.

Changes in conditions of patterns which the scanning lines pass through in this manner corresponds to sub-scanning and are detected as step-shapes. Various correspondence is then possible because the change can be distinguished by signal changes which occur gradually by changing the focal point. For example, in the case of scanning sections "a" and "e", the difference signals for within the scanning lines are extremely small and can be discerned as being no pattern. Meanwhile, movement of the focal point is stopped for the next scanning line and it is rational to execute scanning for the same focal point position. This is because the focusing operation does not function at the scanning sections "a" and "e" for whatever reason. When the scanning section b is entered, a change in the step shape exceeding a threshold value can be seen in the difference signal for the scanning line image. At this time it is detected that the pattern region has been entered from the plain-colored region and comparisons of signals are executed every scanning line while changing the focal point position by a prescribed amount while moving to the next sub-scanning position. The difference signals for between scanning lines at this section are more like small consecutive changes rather than being step-shaped and the focusing operation is then to obtain the peak values for these changes. When scanning section c is entered, the signal again changes to a step shape so that it is detected that a scanning region having a boundary entering from the plain colored region to the patterned region or a scanning region having a boundary exiting from the pattern region to the plain colored region has been entered. At this time, if the signal for the scanning section and the definition of the image are compared, it is possible to double the signal for the scanning section b and make the comparison. Changes in the step shape are typically such that the boundary has increased or decreased by one and consecutive comparison is then possible if correction is performed according to this number. Scanning section d can then be handled in the same way as scanning section b and scanning section e can be handled in the same way as for scanning section a. However, in the present invention, the important thing is to find peak positions for image difference signals between scanning lines. If the peak value is therefore obtained by excluding the scanning sections a and e where there is no pattern and performing comparisons between the sections b, c and d, this position is then the in-focus point. In the scanning method of the present invention, discontinuous points that change into the step-shape occur but adding the correction described previously so as to obtain intercorrelation is not always necessary. The step shape signal changes can be used as a section separating signal and can be made to correspond to operations every section.

In the above description, a description is given assuming inclined scanning composed of horizontal scanning and vertical scanning is implemented using deflection means during beam scanning in order to ensure that the scanning lines reliably pass through a horizontal pattern (scan rotation). However, the main objective is that the beam scanning lines pass through the pattern whether it is a horizontal pattern or a vertical pattern. The same results can therefore also be obtained even when executing a focusing operation where the sample stage is rotated so that the horizontal scanning direction and the horizontal pattern of the sample cross each other.

Figure 2:
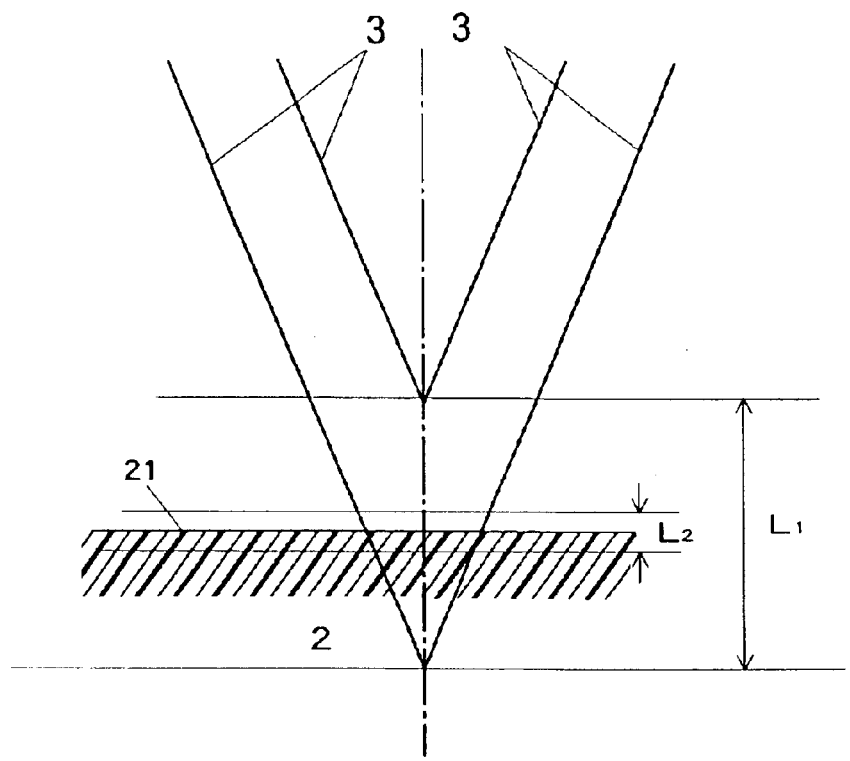
FIG. 2 is a view illustrating the automatic focusing operation of the present invention using a two step method.

Next, a description is given of a method for operating the autofocus of the present invention. In the present invention, the main scanning is executed while changing the focal point for every sub-scanning position. Namely, as shown in FIG. 2, the position of the focal point of the electron beam 3 can be changed from a deep position to a shallow position, with these positions sandwiching the surface position 21 of a semiconductor chip 2 constituting a sample and it is detected at which position the clearest image is obtained. At this time, when the width of the focal positions which are changed every scanning line becomes narrower, the precision of the position specifying the in-focus point (resolution) becomes high, while on the other hand there is the danger that the surface position 21 will not be captured within the width of change. Therefore, in the present invention, as a first step, the width of the focal point positions which are changed for every scanning line is made broad so that the focal point position is changed over a broad focal point region L1 so that the surface position 21 may be reliably caught within this width and the focusing operation is then executed. However, as the width of focal point positions for between scanning lines is broad in this case, rough position information can be obtained in a short period of time but reliable focusing position information cannot be obtained. In a second step, a narrow region L2 reliably including the surface position 21 within it's width is set based on this coarse position information. The width of focal point positions changing every scanning line is then made narrow and the focusing operation is executed once again. It is therefore possible to detect the in-focus point with a high degree of precision because the width of the in-focus point positions for each scanning line during this time is set to be narrow. The focusing operation in the second step access of the present invention is therefore capable of extrapolating the focal point reliably over a broad range to give a precise result over a short time.

Figure 3:
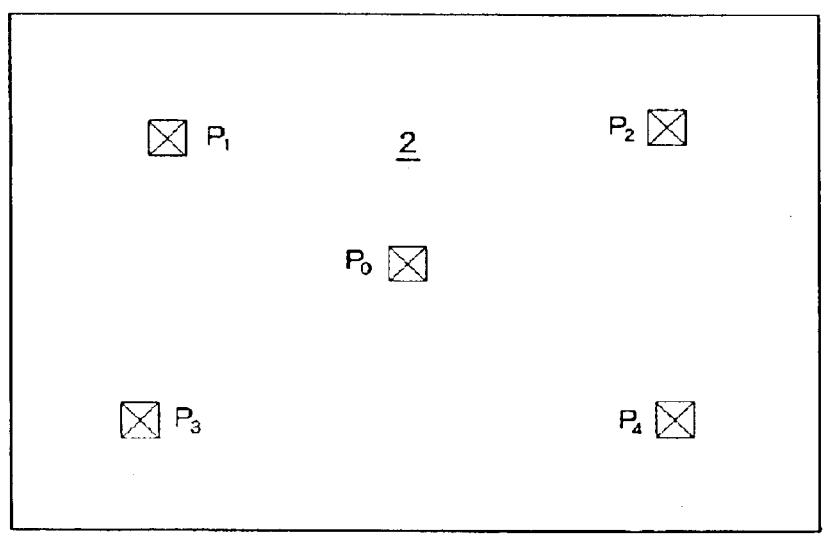
FIG. 3 is a view illustrating the automatic focusing operation of the present invention using an AF point selection registration method.
Figure 4:
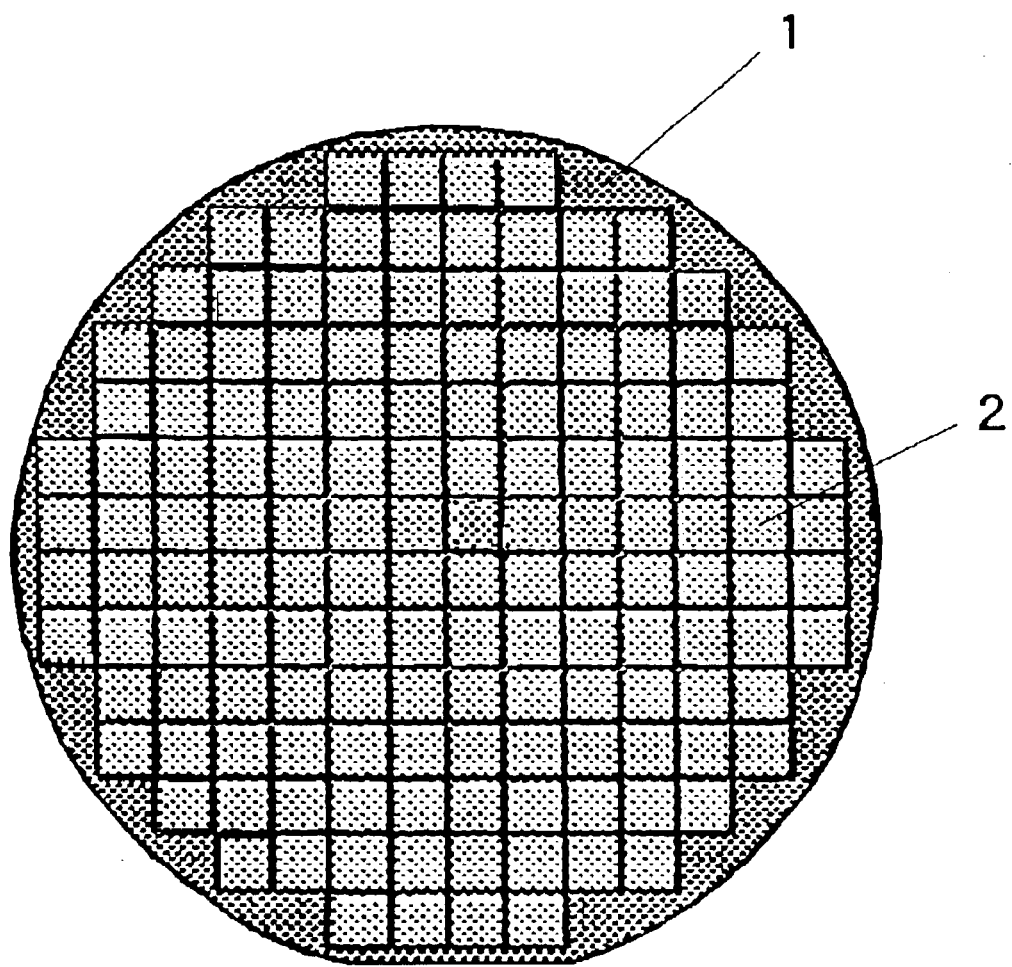
FIG. 4 is a view schematically showing chips formed in an array on a semiconductor wafer.

It cannot be said that the focusing operation for an electron microscope is such that once a focusing position is captured, then this is effective over the whole of the surface of the sample on the stage. Depending on whether the electron microscope is a high-resolution electron microscope, the focal point may be undermined by microscopic undulations and curves in the sample surface or by the operation of the stage drive mechanism. The effectiveness of the obtained in-focus point position information is roughly for around 5 mm. In the case as shown in FIG. 4 where semiconductor chips are arrayed on a wafer, one chip may be 10 mm square or 20 mm square, for example, so that the in-focus point information for one point may not be effective over the whole region. Therefore, in the present invention, a number of locations covering the whole region of the chips are set and a location in the vicinity in which the pattern best suited to a focusing operation exists (hereinafter referred to as an AF point) is selected. When defects within the chip are then monitored, a focusing operation is first carried out at the AF point covering this defect position and the focus value for the lens that is obtained is used during defect observation. Namely, as there are regions within the chip where there is no pattern as well as locations where an AF point cannot be applied, an appropriate location is selected based on the chip pattern and recorded. Examples of AF points ($P_0$, $P_1$, $P_2$, $P_3$ and P4 in the drawings) selected for a chip 2 are shown in FIG. 3. AF points are selected taking into consideration positions that cover the entire region of the chip 2 and the shape of the pattern. The pattern structures for the chips arrayed on the wafer 1 are all the same and the selected points AF may therefore be locations corresponding to each chip respectively. When noted defects are observed based on defect position information provided by a defect checking device, AF points of the chips in the vicinity are first accessed and the focusing operation is executed at these locations. The noted defects are then accessed with the lens at the focusing positioned obtained at this time and monitoring is performed. In this way, AF points applicable to the focusing operation are recorded in advance. This means not only that a reliable focusing operation can be executed, but also that a region where the in-focus point information obtained at the AF points is valid is known. When a plurality of defects then exists within this region, the focusing operation is not repeated each time and defects can be observed consecutively. This is therefore extremely beneficial in that the operation time can be made short.

In the above description, an electron microscope is taken as the object but the present invention can also be applied as is to an ion microscope that is the equivalent to an electron microscope for scanning with a particle beam and detecting secondary charged particles.

The automatic focusing system for a scanning charged particle microscope of the present invention is provided with means for changing a focal point each raster scan line, and control means for comparing image definition each raster line and extrapolating an in-focus point. The focusing operation is therefore dramatically faster compared to the control of related art where the focal point position is changed every frame, image definition is compared every frame, and a in-focus point is then extrapolated. Further, the scanning line is an inclined scanning line that is a combination of a horizontal component and a vertical component with respect to a chip array direction on a semiconductor wafer. A reliable focusing operation can therefore be achieved regardless of the fact that the image region is a horizontal pattern or a vertical pattern.

In the automatic focusing system of the present invention, as a specific method of control for comparing image definition each raster line and extrapolating an in-focus point, scanning sections are distinguished from changes in step shapes for between each scanning line and peak values are extrapolated from small consecutive changes between each scanning line. Therefore, even when the shapes of the patterns through which each scanning lines passes is different, a peak value, i.e. a in-focus point, can be obtained in a reliable and straightforward manner.

Moreover, in the present invention, in a method for implementing automatic focusing control in a scanning charged particle microscope being equipped with means for changing a focal point each raster scan line, and control means for comparing image definition each raster line and extrapolating a in-focus point, there is provided a first step of taking coarse in-focus points using taken large differences between focal points for between scanning lines, and a second step of detecting in-focus points with a high degree of precision using small differences focal points between scanning lines based on the coarse in-focus point information. It is therefore possible to obtain an in-focus point both rapidly and reliably.

Further, a method for implementing automatic focusing control in the present invention comprises the steps of:

recording pre-selected focal points taking into consideration the pattern arrangement of semiconductor chips arrayed on the wafer and being capable of covering the entire region, accessing the in-focus points covering positions of noted defects obtained by a defect checking device and executing a focusing operation, and consecutively monitoring defects in positions covered by the in-focus points in the state of a focal position of a lens obtained at this time. This means not only that a reliable focusing operation can be executed, but also that a region where the in-focus point information obtained at the AF points is valid is known. When a plurality of defects then exists within this region, the focusing operation is not repeated each time and defects can be observed consecutively. This has the benefit that the operation time can be made shorter.

What is claimed is:

1. A scanning charged particle microscope comprising: a charged particle beam source for producing a charged particle beam; a charged particle beam optical system for focusing the charged particle beam; a beam deflecting apparatus for causing the focused charged particle beam to perform raster scanning across a sample having a pattern thereon such that each raster scan line is inclined relative to a direction of a boundary of the pattern; and a control unit for changing a focal point of the focused beam for each raster scan line, comparing an image definition between successive raster scan lines, and determining an in-focus point based on the comparison.

2. A scanning charged particle microscope according to claim 1; wherein the pattern comprises a two-dimensional matrix extending in first and second directions, and each raster scan line is inclined relative to the first and second directions.

3. A scanning charged particle microscope according to claim 1; wherein the sample comprises a semiconductor wafer, the pattern comprises a plurality of semiconductor chips formed on the wafer and arranged in the two-dimensional matrix extending in first and second directions, and each raster scan line is inclined relative to the first and second directions.

4. A scanning charged particle microscope according to claim 1; wherein the control unit discriminates between different scanning sections of the sample based on the number of stepwise changes of an image signal produced by each raster scan line.

5. A scanning charged particle microscope according to claim 1; wherein the control unit first changes the focal point of the focused beam by a relatively larger amount to determine a coarse in-focus point, and then changes the focal point of the focused beam by a relatively smaller amount in the vicinity of the first in-focus point to determine a fine in-focus point.

6. A method for performing automatic focusing in a scanning charged particle microscope which irradiates and scans a charged particle beam over a sample having a pattern thereon and obtains a sample image, comprising the steps of:

scanning the charged particle beam across the pattern in such a manner that each scan line is inclined relative to a boundary of the pattern;

changing a focal point of the charged particle beam for each scan line;

comparing image definition between images obtained for each scan line; and obtaining a position where the clearest image definition is obtained as an in-focus point.

7. A method for performing automatic focusing according to claim 6; wherein the step of scanning the charged particle beam across the pattern comprises scanning the charged particle beam such that successive scan lines are at a broad spacing to obtain a coarse in-focus point, and then scanning the charged particle beam such that successive scan lines are at a narrow spacing narrower than the broad spacing in the vicinity of the range including the coarse in-focus point to obtain a fine in-focus point.

8. A method for performing automatic focusing according to claim 6; wherein the step of comparing image definition between images obtained for each scan line comprises the step of comparing differences between image signals for each scan line at the boundary of the pattern; and the step of obtaining a position where the clearest image definition is obtained comprises the step of obtaining a position at which the differences are at a maximum value.

9. A method for performing automatic focusing according to claim 6; wherein the step of obtaining a position where the clearest image definition is obtained as an in-focus point comprises the step of obtaining an in-focus point at a plurality of areas of the sample; and further comprising the steps of storing the in-focus points; and observing the sample to detect defects using the obtained in-focus points.

10. A method for performing automatic focusing according to claim 6; wherein the pattern comprises a two-dimensional matrix extending in first and second directions, and each scan line is inclined relative to the first and second directions.

11. A method for performing automatic focusing according to claim 6; wherein the sample comprises a semiconductor wafer, the pattern comprises a plurality of semiconductor chips formed on the wafer and arranged in the two-dimensional matrix extending in first and second directions, and each scan line is inclined relative to the first and second directions.

12. A scanning charged particle microscope for irradiating and scanning with a charged particle beam semiconductor chips arranged in a two-dimensional matrix extending in first and second directions on a semiconductor wafer to obtain a sample image, comprising:

scanning means for performing raster scanning of the semiconductor chips with the charged particle beam in such a manner that each scan line is inclined relative to the first and second directions of the semiconductor chips on the semiconductor wafer;

focal point changing means for changing a focal point for each scan line; and control means for comparing an image definition between successive images obtained for each scan line and determining an in-focus point therefrom.

13. A scanning charged particle microscope according to claim 12; wherein the scanning means comprises a beam deflecting apparatus which deflects the charged particle beam in an inclined direction relative to the first and second directions.

14. A scanning charged particle microscope according to claim 12; wherein the control means discriminates between different scanning sections of the semiconductor chips arranged in the two-dimensional matrix based on a number of stepwise changes of the image signal obtained for each scanning line.

15. A scanning charged particle microscope according to claim 12; wherein the focal point changing means changes the focal point by a relatively larger amount to determine a coarse in-focus point, and then by a relatively smaller amount in the vicinity of the range including the first in-focus point to determine a fine in-focus point.

* * * * *